United States Patent [19]

Lee et al.

[11] Patent Number: 4,514,575

[45] Date of Patent: Apr. 30, 1985

[54] PROCESS FOR PREPARING TERTIARY PHOSPHINES

[75] Inventors: John Y. Lee; Dennis P. Bauer, both of Baton Rouge, La.

[73] Assignee: Ethyl Corporation, Richmond, Va.

[21] Appl. No.: 554,901

[22] Filed: Nov. 25, 1983

[51] Int. Cl.$^3$ .............................. C07F 9/50
[52] U.S. Cl. .......................... 568/17; 568/8
[58] Field of Search ..................... 568/8, 17

[56] References Cited

U.S. PATENT DOCUMENTS

| | | | |
|---|---|---|---|
| 3,261,871 | 7/1966 | Fritzsche | 568/17 |
| 3,405,180 | 10/1968 | Natoli | 568/17 |
| 3,780,111 | 12/1973 | Young et al. | 568/8 X |
| 4,131,624 | 12/1978 | Davis et al. | 568/17 |

OTHER PUBLICATIONS

Chemical Abstracts, 62, 10457d, (1965).
Tetrahedron Letters, No. 17, pp. 1157–1162, (1965).
Kosolopoff, Organo Phosphorus Compounds, Wiley-Intersc., N.Y., VI, pp. 45–47, (1972).

*Primary Examiner*—Helen M. S. Sneed
*Attorney, Agent, or Firm*—Donald L. Johnson; John F. Sieberth; Patricia J. Hogan

[57] ABSTRACT

Tertiary phosphine oxides, such as triphenylphosphine oxide, are reduced to the corresponding phosphines with trichlorosilane in an inert halogenated hydrocarbon solvent.

8 Claims, No Drawings

PROCESS FOR PREPARING TERTIARY PHOSPHINES

FIELD OF INVENTION

This invention relates to a process for preparing tertiary phosphines and more particularly relates to such a process wherein a tertiary phosphine oxide is reduced to the corresponding tertiary phosphine.

BACKGROUND

From U.S. Pat. Nos. 3,261,871 (Fritzsche et al. I) and 4,131,624 (Davis et al.); Fritzsche et al. II, CA 62:10457d; L. Horner et al., *Tetrahedron Letters*, No. 17, pp. 1157–1162 (1965); and G. M. Kosolapoff et al., *Organic Phosphorus Compounds*, Vol. 1, Wiley-Interscience (New York), 1972, pp. 45–47, it is known that tertiary phosphine oxides can be reduced to the corresponding phosphines by reaction with trichlorosilane in the presence or absence of an amine catalyst and in the presence or absence of a solvent, such as naphthalene, benzene, toluene, diethylene glycol dimethyl ether, glycol dimethyl ether, or diphenyl oxide.

It would be most desirable to be able to conduct the reaction in the absence of a catalyst and at reaction conditions requiring the least energy expenditure and the lowest possible amount of trichlorosilane. However, as indicated in Fritzsche et al. II, Horner et al., and Kosolapoff et al., it has previously been found necessary to employ at least two mol equivalents of trichlorosilane to reduce a phosphine oxide efficiently in the absence of an amine catalyst. Moreover, Fritzsche et al. II show that the uncatalyzed reduction of triphenylphosphine oxide rerequires reaction of about two mols of trichlorosilane with one mol of the oxide at 200° C. for about two hours to get a phosphine yield of 89.7%.

SUMMARY OF THE INVENTION

An object of this invention is to provide a novel process for reducing tertiary phosphine oxides to the corresponding phosphines.

Another object is to provide an economical process for conducting such a process with trichlorosilane.

These and other objects are attained by reducing a tertiary phosphine oxide with trichlorosilane in an inert halogenated hydrocarbon solvent.

DETAILED DESCRIPTION

Tertiary phosphine oxides utilizable in the practice of the invention are compounds corresponding to the formula:

$$RR'R''PO$$

wherein R, R', and R'' are independently selected from organic groups containing about 1–20 carbons. Generally the organic groups are hydrocarbon groups, e.g., alkyl, alkenyl, cycloalkyl, cycloalkenyl, aryl, alkaryl, or aralkyl groups; and the invention is particularly useful for reducing tertiary aromatic phosphine oxides, such as triphenylphosphine oxide, tritolylphosphine oxide, etc., and tertiary aliphatic phosphine oxides, such as tributylphosphine oxide, trioctylphosphine oxide, etc., to the corresponding phosphines.

As already indicated, the reducing agent of the invention is trichlorosilane, which may be employed in an amount such as to provide about 1–4 mols of reducing agent per mol of oxide. However, it is an advantage of the invention that the trichlorosilane can be used in smaller amounts than were previously found necessary to achieve high yields of phosphine, so it is generally employed in an amount of about 1–2, preferably not more than about 1.5, mols per mol of oxide.

The reaction is conducted in an inert halogenated hydrocarbon solvent, such as chloroform, bromoform, methylene chloride, ethylene dichloride, tertrachloroethylene, 1-chloro-2,2-dimethylpropane, chlorobenzene, etc. Particularly preferred solvents are chloroform and methylene chloride.

The temperatures employed for the reaction can be any temperatures effective for the reduction, e.g., temperatures in the range of about 50°–250° C. However, it is generally most efficient to use temperatures in the range of about 100°–150° C.

The following examples are given to illustrate the invention and are not intended as a limitation thereof.

EXAMPLE I

One molar proportion of triphenylphosphine oxide was reacted with 1.54 molar proportions of trichlorosilane in chloroform at 150° C. and 120 psig for one hour. The reaction resulted in a 100% conversion of the oxide and a 97% yield of triphenylphosphine.

EXAMPLE II

One molar proportion of triphenylphosphine oxide was reacted with 1.58 molar proportions of trichlorosilane in methylene chloride at 150° C. and 150 psig for one hour. The reaction resulted in a 95% conversion of the oxide and a 91% yield of triphenylphosphine.

It is obvious that many variations can be made in the products and processes set forth above without departing from the spirit and scope of this invention.

We claim:

1. A process for converting a tertiary phosphine oxide to the corresponding tertiary phosphine which comprises reacting the tertiary phosphine oxide with a trichlorosilane reducing agent in the presence of an inert halogenated hydrocarbon solvent at a temperature in the range of about 50°–250° C.

2. The process of claim 1 wherein the tertiary phosphine oxide is triphenylphosphine oxide.

3. The process of claim 1 wherein the tertiary phosphine oxide is trioctylphosphine oxide.

4. The process of claim 1 wherein the tertiary phosphine oxide is tributylphosphine oxide.

5. The process of claim 1 wherein the inert halogenated hydrocarbon is chloroform.

6. The process of claim 1 wherein the inert halogenated hydrocarbon is methylene chloride.

7. The process of claim 1 wherein the mol ratio of reducing agent to oxide is about 1.5/1.

8. The process of claim 1 wherein the reduction is conducted at a temperature in the range of about 100°–150° C.

* * * * *